United States Patent [19]
Shimada

[11] Patent Number: 5,916,467
[45] Date of Patent: Jun. 29, 1999

[54] CERAMIC HEATER AND ITS MANUFACTURING METHOD

[75] Inventor: Takeo Shimada, Nitta, Japan

[73] Assignee: Unisia Jecs Corporation, Atsugi, Japan

[21] Appl. No.: 08/743,818

[22] Filed: Nov. 5, 1996

[30] Foreign Application Priority Data

Nov. 8, 1995 [JP] Japan ................................. 7-316126

[51] Int. Cl.$^6$ ................................................... H05B 3/16
[52] U.S. Cl. ........................... 219/543; 219/541; 219/552
[58] Field of Search ................................... 219/543, 542, 219/541, 552, 457; 338/34; 432/241

[56] References Cited

U.S. PATENT DOCUMENTS

| | | | |
|---|---|---|---|
| 4,035,613 | 7/1977 | Sagawa et al. | 219/552 |
| 4,512,871 | 4/1985 | Kato et al. | 204/429 |
| 4,634,837 | 1/1987 | Ito et al. | 219/270 |
| 4,697,165 | 9/1987 | Ishiguro et al. | 338/34 |
| 5,233,166 | 8/1993 | Maeda et al. | 219/552 |
| 5,331,134 | 7/1994 | Kimura | 219/543 |
| 5,573,690 | 11/1996 | Nobori et al. | 219/457 |
| 5,616,024 | 4/1997 | Nobori et al. | 432/241 |
| 5,736,095 | 4/1998 | Shimada et al. | 219/552 |

FOREIGN PATENT DOCUMENTS

| | | |
|---|---|---|
| 195 14 643 A1 | 10/1995 | Germany . |
| 63-146381 | 6/1988 | Japan . |
| 6-235716 | 8/1994 | Japan . |

*Primary Examiner*—Teresa Walberg
*Assistant Examiner*—Vinod D Patel
*Attorney, Agent, or Firm*—Foley & Lardner

[57] ABSTRACT

In a ceramic heater applicable to an oxygen concentration sensor used to detect an oxygen concentration sensor in an exhaust gas of an internal combustion engine, a heating pattern constituted by an electrically resistive body comprises a plurality of radially extended segments on an outer peripheral surface of a cylindrical main body made of a ceramic material. Since a length of an axially extended segment of the heating pattern on the cylindrical main body is excessively short, a tip of a squeege can be prevented from pressing a mask used to make, for example, a curved surface printing using an electrically resistive conductive paste.

9 Claims, 7 Drawing Sheets

CERAMIC HEATER AND ITS MANUFACTURING METHOD

BACKGROUND OF THE INVENTION

The present invention relates to a ceramic heater and its manufacturing method, the ceramic heater being applicable to an oxygen concentration sensor with a heater, the sensor being used to detect an oxygen concentration in an exhaust gas exhausted from a vehicular internal combustion engine.

In general, in an automotive vehicular internal combustion engine on which a turbo charger is mounted, the engine is operated with an air/fuel mixture ratio (air excess rate) which tends to be rich so that a temperature of an exhaust gas from the engine reaches approximately 250° C. However, since a zirconia tube which constitutes a detecting element of the oxygen concentration sensor is normally operated under a temperature around 350° C., the oxygen sensor with the heater is used in the turbo charged internal combustion engine so that the zirconia tube is heated and used as the oxygen concentration sensor.

A Japanese Patent Application First Publication No. Heisei 6-235716 published on Aug. 23, 1994 exemplifies a previously proposed ceramic heater and its manufacturing method.

Although the above-described Japanese Patent Application First Publication describes a curved surface printing of a heating pattern on a ceramic heater main body, a specific form of the heat pattern which indicates a superior, constant heat performance and which indicates a high yield is not described in details, only indicating an axially extended pattern.

Therefore, there is an industrial demand in the manufacture of the ceramic heater that constant resistance value and heat generation quantity can be managed for each manufactured ceramic heater.

SUMMARY OF THE INVENTION

It is an object of the present invention to provide a ceramic heater and its manufacturing method which can achieve a high yield of the ceramic heater with, for example, a curved surface printing and which can provide constant resistance value and heat generation quantity for each manufactured ceramic heater.

According to one aspect of the present invention, there is provided with a ceramic heater comprising:
a cylindrical heater main body formed of a ceramic material and having a curved surface thereon along an axial direction thereof;
an electrically resistive body constituting a heating pattern formed on the curved surface of the heater main body; and
a protective layer arranged so as to enclose the pattern and wherein said pattern comprises a plurality of radially extended segments, said radially extended segments being interconnected one after another.

According to another aspect of the present invention, there is provided a manufacturing method of a ceramic heater comprising the steps of: providing a cylindrical main body formed on a ceramic material and having a curved surface of the heater main body; and providing a protective layer arranged so as to enclose the pattern, and wherein said pattern is formed as to provide a plurality of radially extended segments, said extended segments being interconnected one after another.

BEST MODE FOR CARRYING OUT THE INVENTION

Reference will hereinafter be made to the drawings in order to facilitate a better understanding of the present invention.

Figure 1:
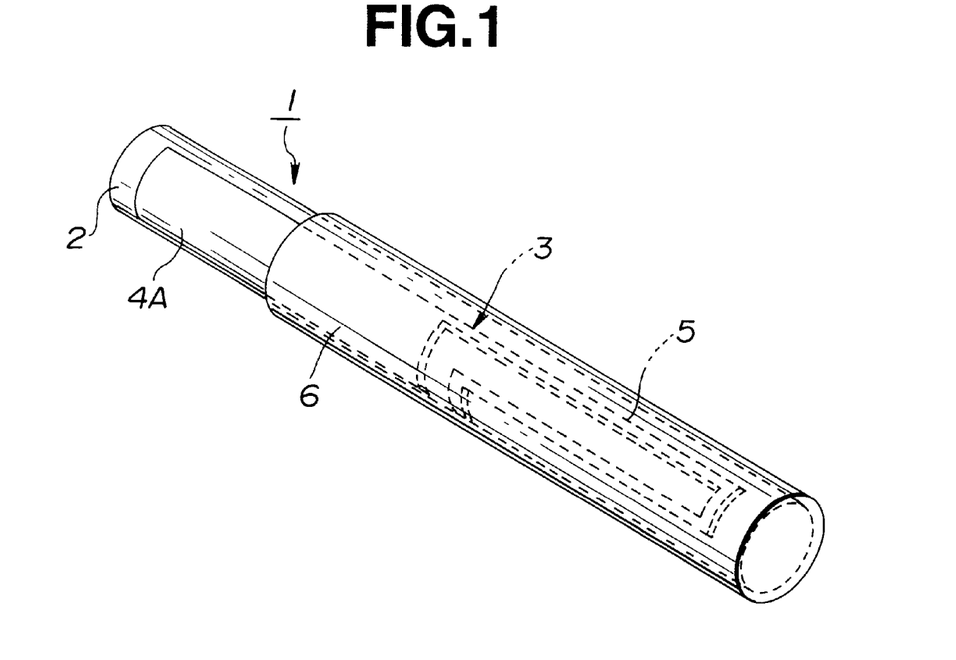
FIG. 1 is a perspective view of a ceramic heater of a comparative example to a first embodiment of the ceramics heater according to the present invention.

FIG. 1 shows a comparative example of a ceramic heater to the ceramic heater in a first preferred embodiment according to the present invention.

Figure 2:
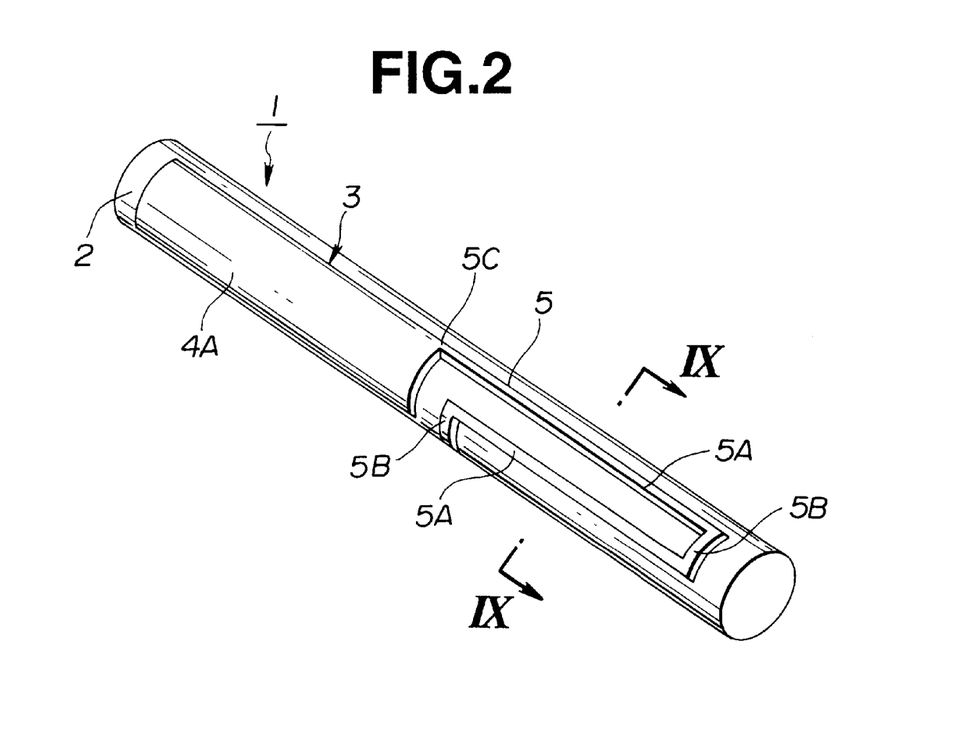
FIG. 2 is a perspective view of a ceramic heater of the comparative example shown in FIG. 1 to a first embodiment of the ceramics heater according to the present invention (with a protective layer omitted).

FIG. 2 shows the comparative example of the ceramic heater to that in the first preferred embodiment with a protective layer omitted.

In the comparative example of FIGS. 1 and 2, a ceramic heater 1 includes a cylindrical heater main body as a mother material of the ceramics heater 1. The heater main body 2 is manufactured in the following method. That is to say, a rod-shaped heater core is formed by drying and solidifying the rod-shaped heater core which has been treated under an injection molding or an extrusion process from a ceramic material such as an alumina and which thereafter has been cut by a predetermined length. The heater main body 2 is formed as the cylindrical rod having, for example, an outer diameter of about 3.8 mm and a length of about 57 mm.

In FIGS. 1 and 2, a heating pattern 3 is printed by means of a screen printer 11 (as will be described later) arranged over an outer peripheral surface of the heater main body 2.

An electrically conductive paste 13 made of a heat generative electrically conductive material such as a tungsten (W) is printed and applied to form a predetermined film thickness (for example, 40 μm). The heating pattern 3 includes a pair of leading electrode patterns (portions) 4A and 4B formed on a lateral side in an axial direction of the main body 2 which is a basic end of the heater main body 2, and a heater portion 5 electrically connected to the leading electrode portions 4A and 4B and located at the other lateral side in the axial direction of the main body 2. The heater portion 5 is constituted by six straight line (major axially extended) portions 5A, 5A, - - - extended in the axial direction and by five connective portions 5B, 5B, - - - radially and straightly extended and bent to connect the respective five straight line portions 5A.

Figure 3:
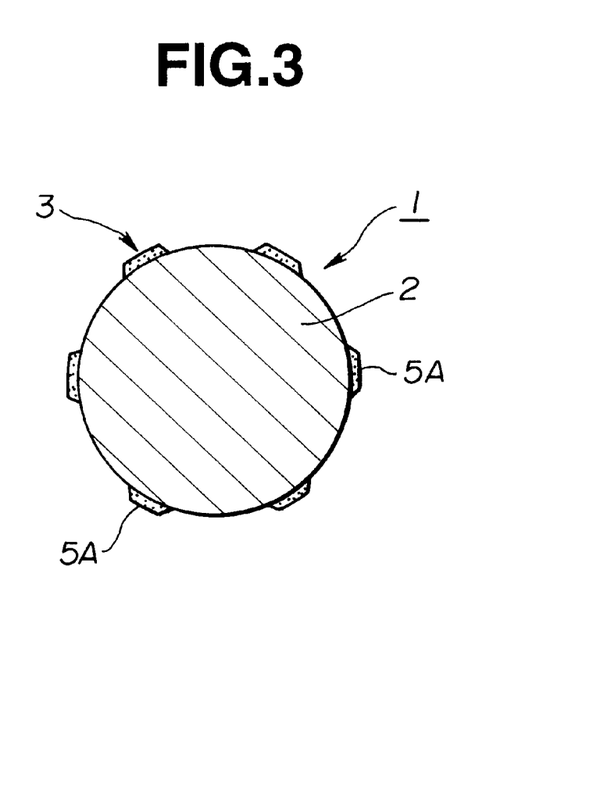
FIG. 3 is a cross sectional view of the ceramic heater of the comparative example shown in FIGS. 1 and 2 to the embodiment of the ceramic heater according to the present invention which is cut away along a line IX—IX of FIG. 2.
Figure 4:
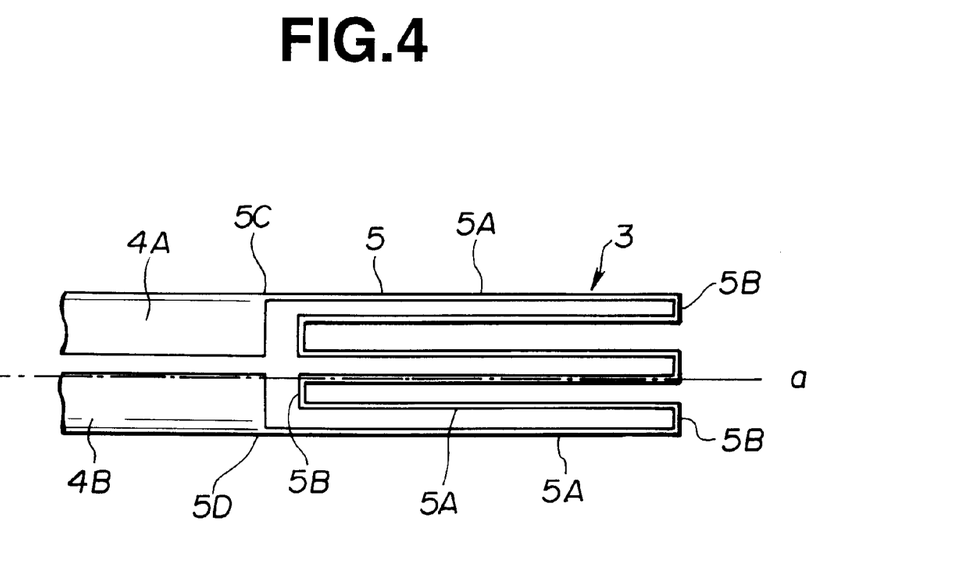
FIG. 4 is a top view of a heating pattern in the comparative example shown in FIGS. 1 to 3.

FIG. 3 shows a longitudinally cross sectional view of the ceramic heater in the comparative example cut away along the line IX—IX of FIG. 2 and FIG. 4 shows the heating pattern in the comparative example of FIGS. 1 to 3. A part of the respective straight line portions 5A which is interconnected between one of the pair of electrode portions 4A and one of the respective straight line portions 5A is denoted by (start point) 5C. A part of the respective straight line portions 5A which is interconnected between the other of the pair of electrode portions 4A and one of the respective straight line portions 5A is denoted by (end point) 5D.

The protective layer 6 is formed on an outer peripheral surface of the main body 2 to protect the heating pattern 3. After a curved surface printing is carried out to form the heating pattern 3, the heating pattern 3 is immersed within a slurry ceramics such as alumina so that a slurry casting is carried out on the outer periphery of the heating pattern 3.

Figure 5:
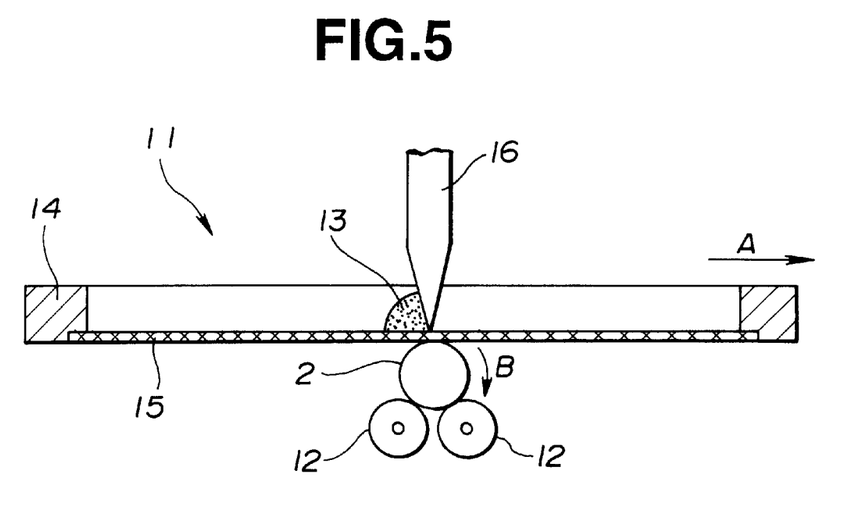
FIG. 5 is an explanatory view of printing by means of a screen printer to which the ceramic heater according to the present invention is applicable.
Figure 6:
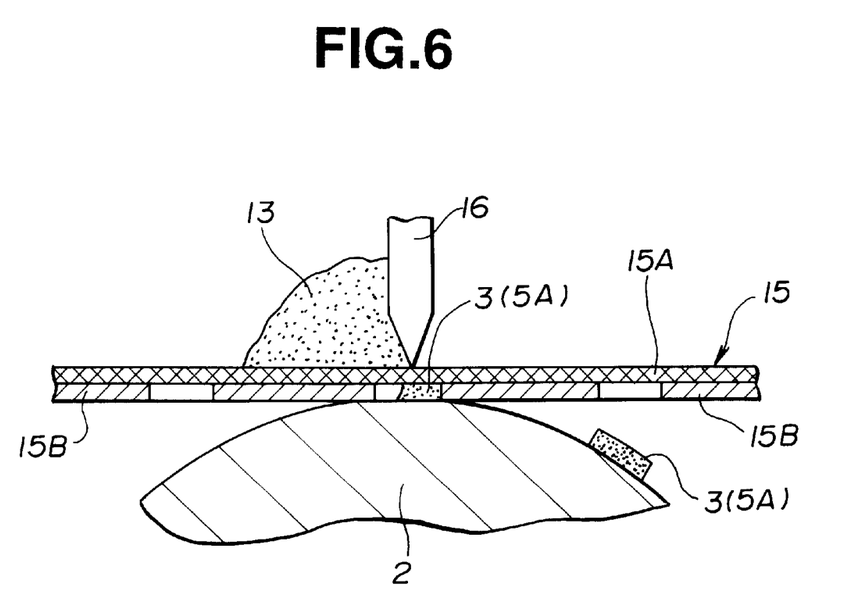
FIG. 6 is an explanatory side view of the heating pattern which is printed by the screen printer.

FIGS. 5 and 6 shows the manufacturing method of the ceramic heater in the comparative example.

First, the main body 2 is formed in the cylindrical (rod) shape by means of an injection molding or extrusion, and, thereafter, by means of a cutting of the ceramic main body serving material by a predetermined length.

Thereafter, the main body 2 is sufficiently dried and solidified and then a curved surface printing is carried out on the outer peripheral surface of the main body 2. In this case, the electrode patterns (portions) 4A and 4B of the heating pattern 3 are extended at the basic end of the heater main body 2.

Next, the main body after the curved surface printing is immersed into the slurry ceramics such as the alumina ceramics and the protective layer 6 is under the slurry casting on the outer periphery of the printed heating pattern 3. Then, both of the protective layer 6 and the heater main body 2 are fired, for example, under an atmosphere of a reducing gas. Thereafter, in a metal treatment process, electrically conductive materials are metal processed on the parts of the electrode portions 4A and 4B exposed externally to form terminals (not shown) in order for the heating pattern 3 to be supplied with a power. Thus, the ceramics heater 1 is manufactured.

The curved surface printing is carried out as shown in FIG. 5. In FIG. 5, the screen printer 11 is used for the curved surface printing and is provided with a pair of (rollable) rollers 12 and 12 on each of which the heater main body 2 is mounted to form the heating pattern 3 on he peripheral surface of the heater main body 2.

In this case, with an axial center of the main body 2 on a chuck (not shown) fixed, the main body 2 is rotated with the fixed axial center as a center so that an electrically conductive paste 13 is printed on the outer peripheral surface of the heater main body 2 to form the heating pattern 3.

The screen printer 11 includes a mask 15 held by means of a mask frame 14 in a square form and a squeege 16 arranged on the mask 15 and made of a synthetic resin such as a polyurethan. The mask 15 includes a mesh 15A and an emulsifier 15B adhered onto an underside surface of the mesh 15A. The printing pattern corresponding to the heater pattern 3 by means of the emulsifier 15B is formed on the mesh 15A. Then, during the printing, the mask 15 is moved in an arrow-marked direction in FIG. 5 together with the mask frame 14 and the squeege 16 is used to rake the electrically conductive paste 13 supplied on the mask 15 so that the heating pattern 3 is formed during the curved surface printing.

At this time, the heater main body 2 arranged between the respective rollers 12 and the mask 15 is rotated in another arrow-marked direction B (shown in FIG. 5) in accordance with the rolling movement of the rollers 15. Thus, the part of the conductive paste 13 raked by means of the squeege 16 is transcribed over the outer peripheral surface of the heater main body 2. Then, the heater pattern 3 is formed as a uniform film thickness over an outer peripheral surface of the heater main body 23 ranging from the basic end shown in FIG. 2 to the tip end of the heater main body 2.

Next, a detecting operation of the oxygen concentration in the case where the heater equipped oxygen concentration sensor is actually mounted in a vehicle.

At first, the heater mounted oxygen concentration sensor is installed into an exhaust gas tube of the automotive vehicle and is fixed into the exhaust gas tube so that a tip end of the zirconia tube which serves as the detecting element of the sensor is projected into the exhaust gas tube.

Then, when the exhaust gas flows into the exhaust gas tube during the running of the vehicular engine and is introduced into a surrounding of the zirconia tube, the oxygen concentration of the exhaust gas causes an electromotive force on the zirconia tube since the large difference in the concentration of oxygen occurs between the exhaust gas oxygen component and the atmospheric pressure. Thus, the electromotive force is generated in the zirconia tube and is outputted to an external control unit as a detection signal. The control unit is used to manage an air-fuel mixture ratio of an air-fuel mixture supplied to the engine.

The oxygen concentration sensor with the ceramics heater is exemplified by a U.S. patent application Ser. No. 08/426, 121 filed on Apr. 20, 1995 (the disclosure of which is herein incorporated by reference).

In addition, since the ceramic heater 1 receives the power supply external via lead lines and contact springs (not shown), the heater main body 2 serves to heat an internal side of the zirconia tube together with the heating pattern 3 as a heat source so that the zirconia tube is activated and is raised up to the temperature about 350° C. so as to compensate for the output of a normal detection signal from the zirconia tube.

The plurality of elongated straight line portions a in the direction denoted by the dot-and-dash lines of FIG. 4 (for example, six) are present in the direction orthogonal to the direction along which the squeege 16 is moved with respect to the mask 15 during the curved surface printing. Due to the presence of this shape, when the curved surface printing is carried out as described above, a tip of the squeege 16 is pressed down on the mesh 15A so as to be brought in close contact with the heater main body 2.

In details, as shown in FIG. 6, when a force pressing the mask 15 is appropriate, the squeege 16 is moved slightly pressing a surface of the mesh 15A. At this time, the squeege 16 causes the conductive paste 13 to be pushed out in a space having a rectangular shape of cross section serving as a print pattern and formed inbetween the mask 15 and heater main body 2. Consequently, the printing is carried out having a sufficient thickness (for example, approximately 40 μm) to the heater pattern 3 (straight line portion 5A). Then, even after the heat is applied to the subsequent firing process, the heating pattern 3 having the sufficient film thickness as shown in FIG. 3 can be formed.

Figure 7:
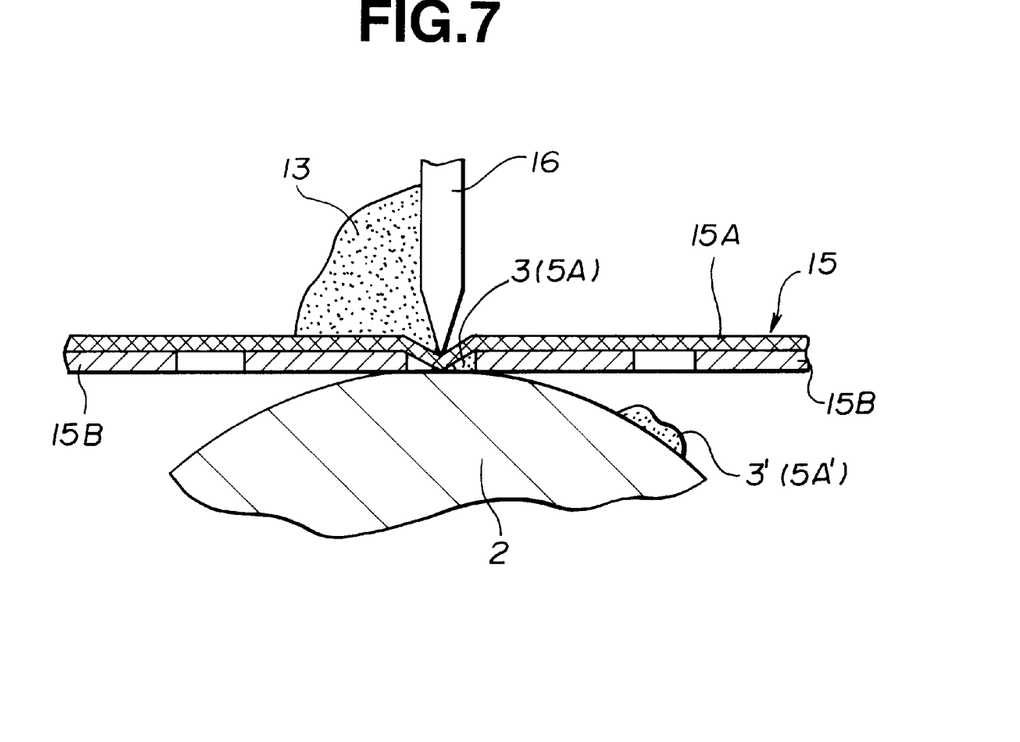
FIG. 7 is an explanatory side view of the heating pattern which is printed by the screen printer as not a preferable form.
Figure 8:
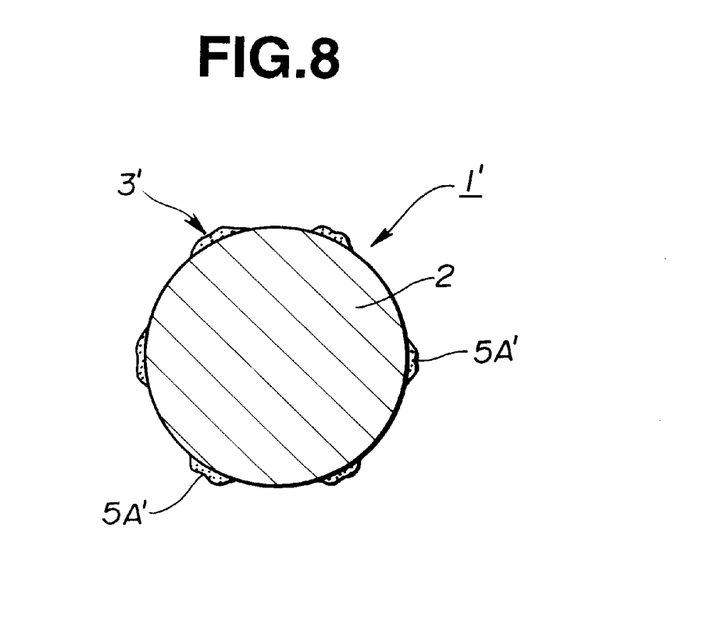
FIG. 8 is a longitudinal cross sectional view of the ceramic heater manufactured by the screen printer in FIG. 7.

However, as shown in FIG. 7, when the force from the squeege 16 to press the mask 15 is excessively large, the squeege 16 moves in the state wherein the surface of the mesh 15A is greatly pressed. Therefore, the tip of the squeege 16 presses the part of the mesh 15A located between the emulsifiers 15A and 15B toward the heater main body 2, the cross section serving as the print pattern formed between the mask 15 and the heater main body 2 has the space in the rectangular shape having the upper surface recessed. At this time, since the conductive paste 13 printed is formed so as to be the elongated rectangular shape, the heater pattern 3' (straight line pattern 5A') cannot provide the printing of the sufficient film thickness. Thus, after the heat is applied at the subsequent firing process, the small (recessed) heater pattern 3' (straight line portion 5A') is formed as the minor heating pattern 3' (straight line portion 5A') having the small (recessed) cross section as shown in FIG. 8 is formed.

Since, in the comparative example, the print pattern 3 having the longer axially extended portions of the heater main body 2 is formed during the curved surface printing, the film thickness of the heating pattern 3 according to the strength of pressing force applied from the squeege 16 to the mask 15 is varied so that the film thickness of the heating pattern 3 cannot uniformly be formed. Furthermore, since the film thickness of the heating pattern 3 cannot be formed constant, a resistance value and heat generated quantity cannot be managed uniformly for each ceramic heater 1 manufactured.

Thus, it is discovered that if the number of times the squeege 16 is moved along the axial direction of the heater main body are reduced (or eliminated), the heating pattern having no (almost no) presence of the axially extended (straight line) segments can be formed and this means that the each ceramic heater having constant resistance value and constant heat generation quantity of the heating pattern can be achieved and manufactured with a high yield.

FIGS. 9 through 14 show respectively the ceramic heater 21 manufactured according to the present invention.

Figure 9:
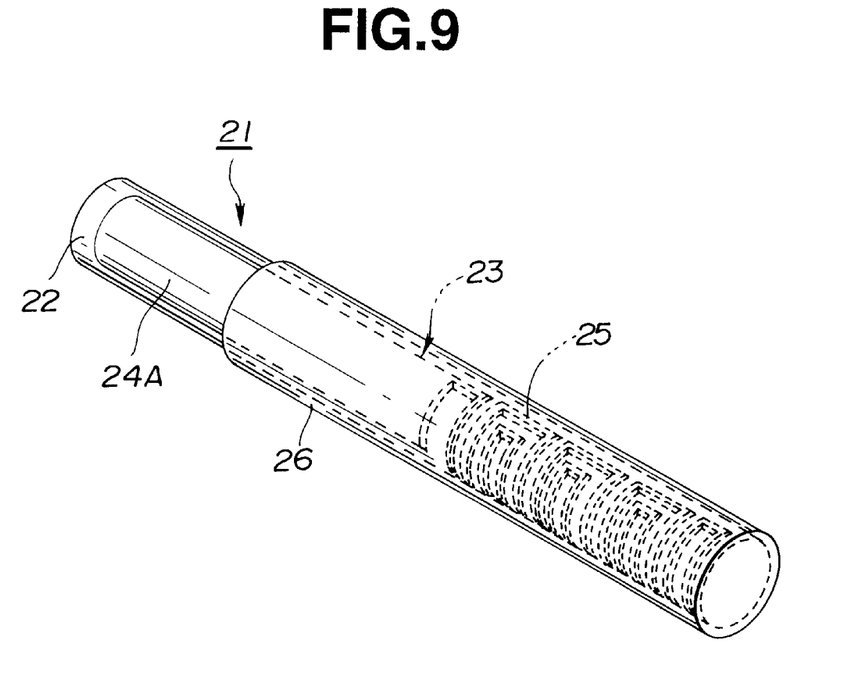
FIG. 9 is a perspective view of the ceramic heater in the first preferred embodiment according to the present invention.
Figure 10:
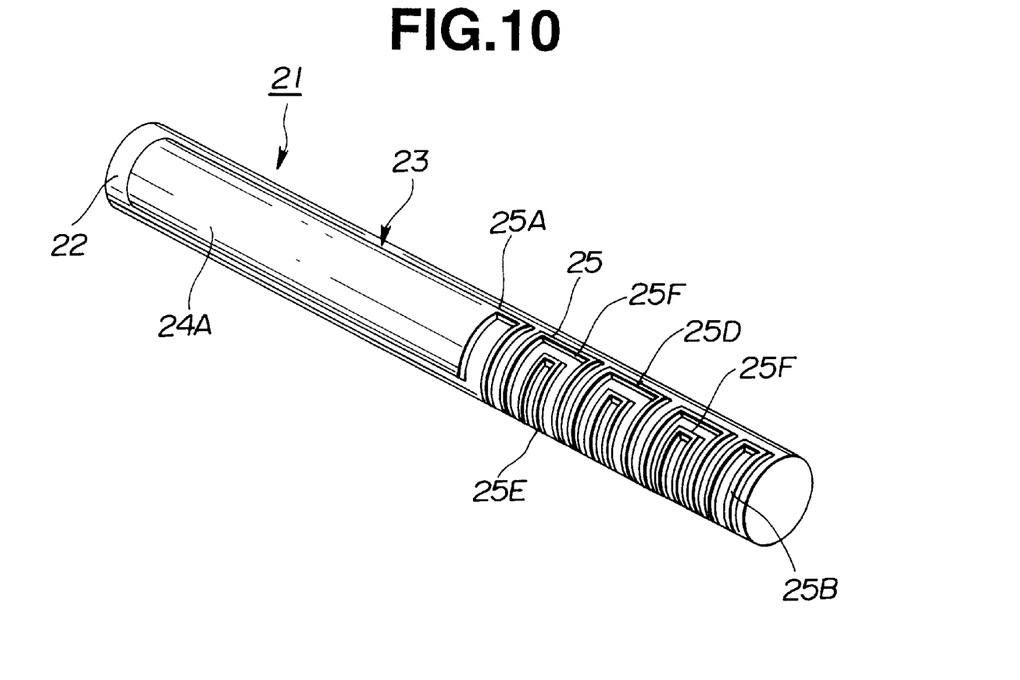
FIG. 10 is a perspective view of the ceramics heater in the first embodiment shown in FIG. 9 before the manufacture of a protective layer on the heating pattern of FIG. 9.
Figure 11:
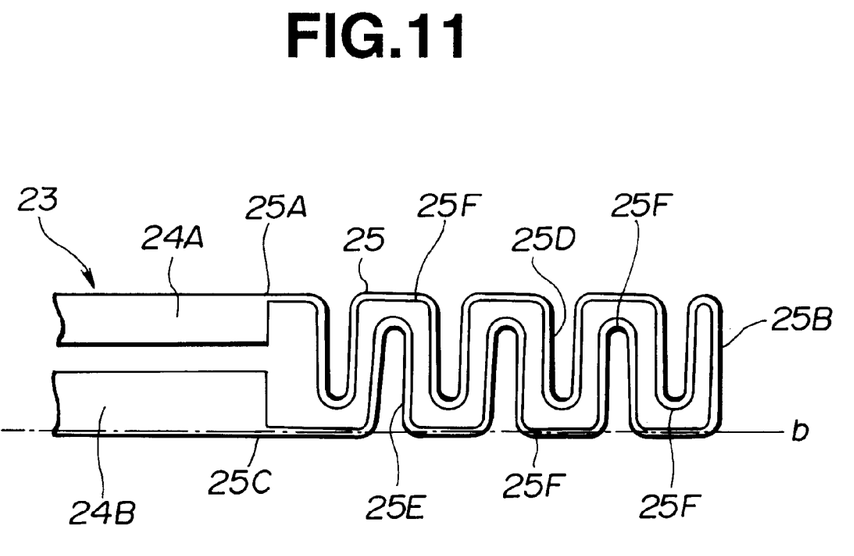
FIG. 11 is a plan view of the heating pattern in the first preferred embodiment of the ceramic heater according to the present invention.

FIGS. 9 through 11 specifically show the first preferred embodiment of the ceramic heater 21 according to the present invention.

In FIGS. 9 through 11, the ceramic heater 21 in the first embodiment includes the ceramic heater main body 22 as the mother material of the ceramic heater 21. The heater main body 22 is formed as the heater core in the rod shape by drying and solidifying the rod shaped heater main body 22 after the injection molding or extrusion from the ceramic material made of the alumina in the same way as described in the comparative example and thereafter by cutting the rod shaped main body 22 by the predetermined length to form the rod shaped heater core.

The heating pattern in the first embodiment is denoted by 23. The heating pattern 23 is formed by being printed in the curved surface printing on the outer peripheral surface of the heater main body 22 so that the conductive paste 13 made of the heat generative conductive material such as the tungsten (W) is printed and formed on the outer peripheral surface of the heater main body 22. The heating pattern 23 includes the pair of lead electrode portions 24A and 24B formed on the outer peripheral surface of the heating main body 22 at its basic end in the axial direction, the, so-called, zigzag (more specifically called, a meander portion since there is no sharp turn) shaped heating portion 25 electrically connected between the lead electrode portions 24A and 24B.

As shown in the elevational view of FIG. 11, with the junction part of the zigzag shaped heating portion (heating segments) 25 as the start point 25A which serves as the basic end of the heater main body 22, the other end of the tip of the axially extended segment serves as the folding point 25B, an outward going road 25D between the start point 25A and the folding point 25B and a returning road 25E between the folding point 25B and the end point 25C formed, respectively. In addition, a plurality of meander portions 25F, 25F, - - - , are formed in a sinusoidal waveform shape having a plurality of larger radii of curvatures between the outward going road 25D and the returning road 25E.

As shown in FIG. 11, the rate of the radially extended segments 25D, 25B to the axially extended segments 25F in the heating pattern 25 is considerably large and each meander portion 25F in the outward going road 25D and each meander portion 25F of the returning road 25E are mutually adjacent to each other to form a pair of integrated heating patterns mutually faced with each other.

Therefore, since the zigzag shaped heater portion 25 is formed in the sinusoidal waveform with a single line having the plurality of meander portions 25F, 25F, - - - from the start point 25A up to the end point 25C, the axially extended segment in the axial direction of the heater main body 22 is actually not present and the radially extended segments are occupied in the heating pattern.

The protective pattern 26 is formed on the outer peripheral surface of the heater main body 22 in order to protect the heating pattern 23. After the heating pattern 23 is printed in the curved surface printing, the heating pattern 23 is immersed into the slurry ceramic such as the alumina so as to carry out a slurry casting on the outer periphery of the heating pattern 23.

It is noted that even in the ceramic heater 21 thus manufactured, the same detection operation of the heater equipped oxygen concentration sensor can be achieved as described in the case of the comparative example.

Since the ceramic heater 21 in the first embodiment includes the heater portion 25 of the heating pattern 23 comprising the outward going road 25D having the plurality of meander portions 25F, 25F, - - - extended from the start point 25A up to the folding point 25B and the returning road 25E having the plurality of meander portions 25F, 25F, - - - extended from the folding point 25B up to the end point 25C, the outward going road 25D starting from the one of the pair of electrode portions 25E ending at the other of the pair of electrode portions 24B, the elongated straight line portions which are long in the axial direction of the heater main body 22 but the elongated straight line portions which are comparatively short (or excessively short) are present even on a straight line b denoted with a dotted line shown in FIG. 11. Therefore, the mask 15 used in the curved surface printing to point the heating pattern 23 has no print pattern having the elongated straight line portion extended in a direction orthogonal to the direction toward which the squeege 16 is moved with respect to the mask 15.

Hence, when the curved surface printing is carried out in the same way as shown in FIG. 5 during the manufacturing process of the ceramic heater 21 in the first embodiment and the force pressing the squeege 16 toward the heater main body 22 is considerably large, the print pattern extending in the direction orthogonal to the direction toward which the squeege 16 is moved with respect to the mask 15 is not present so that the space in the rectangular shape of cross section which provides the printed pattern formed by the mask 15 and the heater main body 22 can be prevented from being disrupted (crushed) by the tip of the squeege 16.

Consequently, the conductive paste 13 is pushed out in the space in the rectangular shape by means of the squeege 16 so that the heating pattern 23 is printed on the outer peripheral surface of the heater main body. At this time, the heating pattern 23 printed on the outer peripheral surface of the heater main body is formed so that the conductive paste 13 is formed in the rectangular shape of cross section. Therefore, the printing having the sufficient thickness is carried out (for example, approximately 40 $\mu$mm). In this way, since, in the ceramic heater 21 in the first embodiment, the shape of the heating pattern 23 formed on the outer peripheral surface of the heater main body 22 is of the generally zigzag shape having the radially extended segments of the heater main body with the respective meander portions 25F, the squeege 16 used in the curved surface printing can eliminate the printing pattern extended in the axial direction toward which the squeege 16 is moved on the mesh 15.

Thus, the tip of the squeege 16 can be prevented from pushing onto the mask 15 so that the film thickness of the heating pattern 23 can be set constantly irrespective of the pressing force from the squeege 16. Consequently, the resistance value and heat generation quantity of the heating pattern 23 of the ceramic heater 21 can be managed to always indicate the constant values, the improvement in the quality of the manufactured ceramic heater can be achieved (,i.e., a yield of the ceramic heater can be increased).

Next, FIGS. 4, 5, and 6 show second, third, and fourth preferred embodiments of the ceramic heater.

Figure 12:
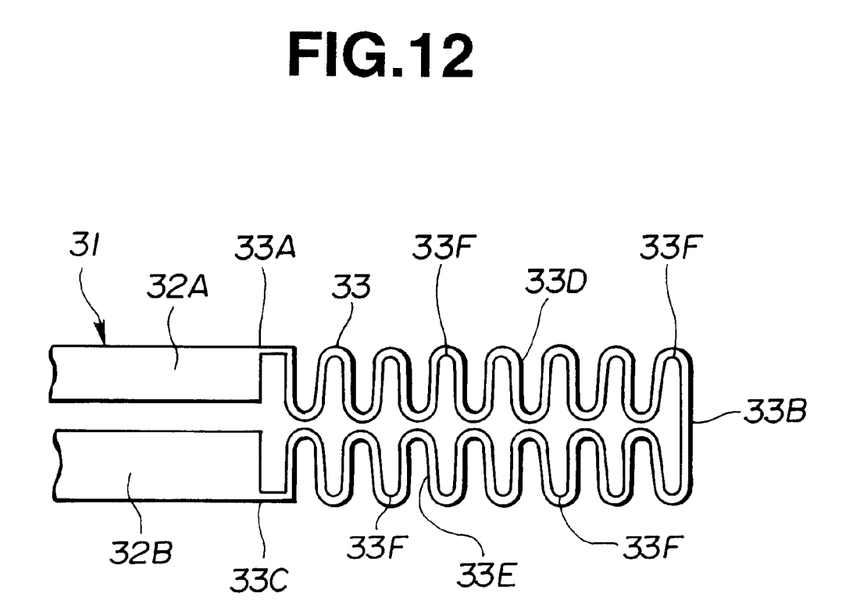
FIG. 12 is a plan view of the heating pattern in a second preferred embodiment of the ceramic heater according to the present invention.

In FIG. 12, the heating pattern 31 in the second embodiment is formed through the curved surface printing on the outer peripheral surface of the heater main body 22. Hence, the heating pattern 31 includes the pair of lead electrode portions 32A and 32B formed and located at a side in the axial direction of the heater main body 22 which is the basic end of the heater main body 31 and the zigzag shaped heating portion 33 which provides the zigzag shaped pattern connected electrically between the pair of the electrode portions 32A and 32B.

The zigzag shaped heating portion 33 in the second embodiment is divided into the outward going road 33D, the returning road 33E, and the waveform shaped heating patterns mutually shaped so as to face with each other.

Thus, the zigzag shaped heating pattern 33 is formed in the zigzag shape by a single line having the plurality of meander portions 33F, 33F, - - - from the start point 33A to the end point 33C, There is provided with the zigzag shaped heater portion 33 in which the long axially extended portions (straight line portions) in the axial direction are not present and in which the radially extended segments are occupied.

Figure 13:
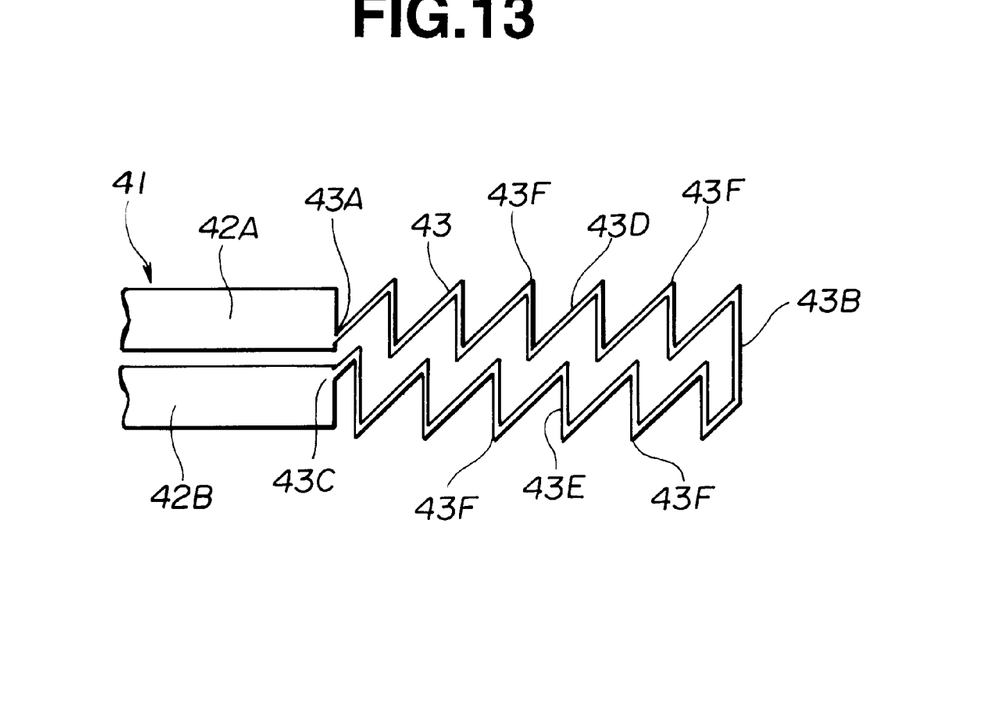
FIG. 13 is a plan view of the heating pattern in a third preferred embodiment of the ceramic heater according to the present invention.

The zigzag shaped heater portion 43 in the third embodiment according to the present invention is located between the pair of the electrode portions 42A and 42B.

The part of one of the pair of electrode portions 42A located at one side in the axial direction which is the basic end of the heater main body 22 is the start point 43A. The other side in the axial direction which is the tip of the heater main body 22 is the folding portion 43B. The part connected to the other side in the axial direction is the end point 43C. The outward going road 43E from the folding point 43B up to the end point 43C and the returning road 43E formed from the returning point 43B to the end point 43C are formed respectively. The plurality of meander portions 43F, 43F, - - - radially extended in a mountain form are formed.

In addition, the zigzag shaped heater portion 43 in the third embodiment is formed in the mountain shape having obliquely slanted portions 43F formed between the outward going road 43D and the returning road 43E.

Hence, the outward going road 43D and the returning road 43E are formed adjaciently spaced apart.

The zigzag shaped heater portion 43 in the third embodiment is formed so as to have the zigzag shape by means of the single line constituting the plurality of meander portions 43F, 43F, - - - . The zigzag shaped heater portion 43 is formed in which the long straight line portions in the axial direction are not present.

Figure 14:
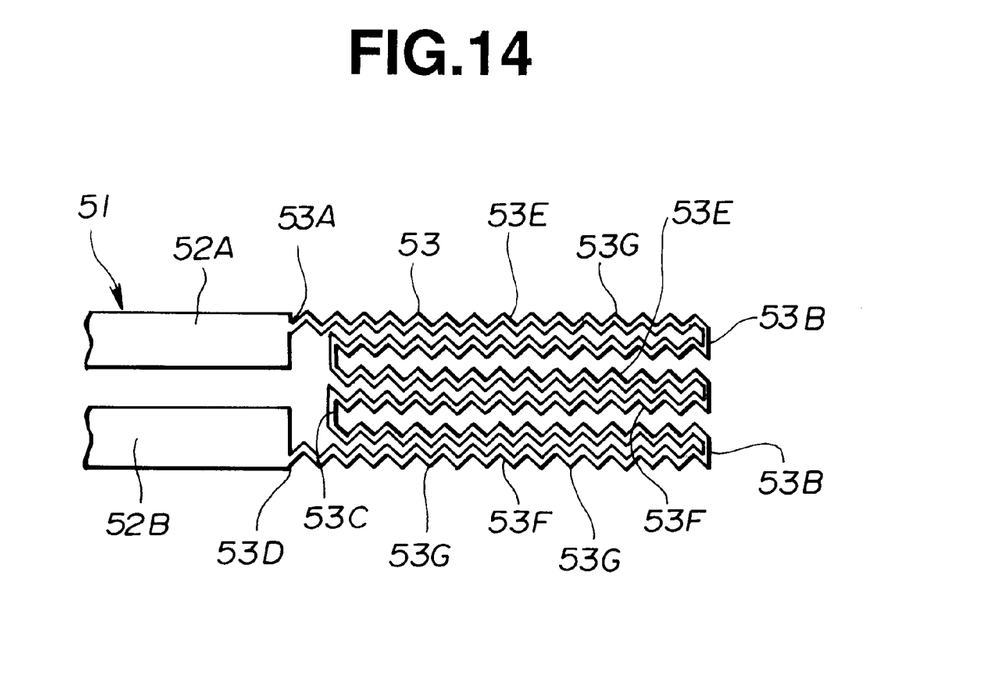
FIG. 14 is a plan view of the heating pattern in a fourth preferred embodiment of the ceramic heater according to the present invention.

The heater pattern 51 in the fourth embodiment is formed by means of the curved surface printing on the outer peripheral surface of the heater main body 22. The heater pattern 51 in the fourth embodiment is formed by means of the curved surface printing on the outer peripheral surface of the heater main body 22. The heater pattern 51 includes the pair of the lead electrode portions 52A and 52B formed at one side in the axial direction which is the basic end of the heater main body 22 and the zigzag shaped heating pattern 53 electrically connected between the pair of the lead electrode portions 52A and 52B.

As shown in FIG. 14, the zigzag shaped heater portion 53 has the start point 53A connected to the part of the pair of the electrode portions 52A located at the side of the axial direction which is the basic end of the heater main body 22, the folding point 53B located at the other side in the axial direction which is the tip of the heater main body 22, and the end point 53D connected to the other of the pair of the electrode portions 52B located at the other side of the axial direction. The plurality of (three) outward going roads 53E, 53E, 53E are formed between the one side of the axial direction and the other side of the returning roads 53F, 53F, and 53F. The plurality of meander portions 53G, 53G, - - - are formed in a plurality of triangular shapes between the respective outward going roads 53E and the respective returning roads 53F.

In this way, the zigzag shaped heater portion 53 is formed by the single line having the triangular shapes meandered in the radial direction. Therefore, the heater pattern 51 is formed in the zigzag shape having the single line of radially extended components from the start point 53A to the end point 53D. Hence, almost no straight line portion extended in the axial direction is present.

In each of the heating patterns 31, 41, and 51 of the respective embodiments, the elongated printing pattern which is extended in the axial direction is not required on the mask 15 so that the space having the rectangular shape of cross section constituting the print pattern formed between the mask 15 and the heater main body 22 by the tip of the squeege 16 during the curved surface printing can be prevented from being disrupted. Hence, the conductive paste 13 is pushed on this space so that the printing of a sufficient film thickness can be carried out to achieve the heating patterns 31, 41, and 51.

Hence, the film thickness of the heating pattern 31, 41, or 51 can be managed at constant and the resistance value and heat generation quantity thereof can always be managed to be constant. Consequently, the rate of failure in the product of the ceramic heater can be improved.

It is noted that the heating pattern is not limited to the respective embodiments shown in FIGS. 11, 12, 13, and 14 but may be formed in the shape in which almost no or no presence of the straight line portion(s) extended in the axial direction occurs.

It is noted that although the present invention is applicable to the curved surface printing but may be applied equally well to a flat surface printing.

Furthermore, the heating pattern in each preferred embodiment 23, 31, 41, and 51 is formed of the heat generative conductive material such as the tungsten (W). However, the heating pattern may be made of another heat generative conductive material, for example, a Platinum (Pt) or Molybdenum (Mo). It is noted that in the case of the use of the Platinum, the firing process may be carried out under the atmospheric pressure.

What is claimed is:

1. A ceramic heater comprising:
   a cylindrical unitary main body formed of a ceramic material and having a curved surface thereon along an axial direction thereof;
   a pair of axially elongated foil form electrode patterns both of which are formed on the curved surface of the unitary main body at a same end portion of the unitary main body in the axial direction thereof;
   an electrically resistive pattern comprising a heating pattern formed directly on the curved surface of the main body, wherein the heating pattern interconnects said electrode patterns and wherein the heating pattern forms an approximately zigzag or meander shape from one electrode to the other electrode; and
   a protective layer so arranged as to enclose the pattern.

2. A ceramic heater according to claim 1, wherein said heating pattern further comprises:
   first and second extending portions, wherein each extending portion has proximal and distal ends; wherein
      the proximal end of said first extending portion is interconnected with one of said pair of electrode patterns; and
      the proximal end of said second extending portion is interconnected with another of said pair of electrode patterns; and
      the distal ends of first and second extending portions are interconnected.

3. A ceramic heater according to claim 1, wherein the distal ends of the first and second extending portions are interconnected by a radially extending portion.

4. A ceramic heater according to claim 1, wherein said first and second extending portions are approximately a zigzag shape.

5. A ceramic heater according to claim 1, wherein said first and second extending portions are approximately a meander shape.

6. A ceramic heater according to claim 1, wherein said heating pattern comprises:
   first and second extending portions having approximately zigzag or meander shape, wherein each extending portion has proximal and distal ends; wherein
      the proximal end of said first extending portion is interconnected with one of said pair of electrode patterns; and
      the proximal end of said second extending portion is interconnected with the other of said pair of electrode patterns; and
      said distal ends of said first and second extending portions are interconnected by a plurality of alternately extending portions; and
   wherein the first and second extended portions together with the alternately extending portions form a continuous pattern.

7. A ceramic heater according to claim 1, wherein said heating pattern is printed onto the curved surface of the heater main body with a screen printer.

8. A ceramic heater according to claim 1, wherein the ceramic heater is applied to an oxygen censor installed in an internal combustion engine.

9. A method for making a ceramic heater comprising:
   providing a cylindrical unitary main body formed of a ceramic material and having a curved surface thereon along an axial direction thereof;
   forming a pair of axially elongated foil form electrode patterns on the curved surface of the unitary main body, wherein both of said electrode patterns are formed at a same end portion of the unitary main body in the axial direction thereof;
   forming an electrically resistive pattern comprising a heating pattern directly on the curved surface of the main body, wherein the heating pattern interconnects said electrode patterns and wherein the heating pattern forms an approximately zigzag or meander shape from one electrode to the other electrode; and
   providing a protective layer so arranged as to enclose the heating pattern.

* * * * *